United States Patent [19]
Ryan et al.

[11] Patent Number: 5,880,297
[45] Date of Patent: Mar. 9, 1999

[54] PROCESS FOR THE PURIFICATION OF GLYCIDYL ESTERS FROM EPIHALOHYDRIN AND CARBOXYLIC ACIDS

[75] Inventors: Richard William Ryan, Kingwood, Tex.; Gerald G. McGlamery, Jr., Baton Rouge, La.; Ralph Martin Kowalik, Kingwood, Tex.

[73] Assignee: Exxon Chemical Patents Inc., Houston, Tex.

[21] Appl. No.: 861,408

[22] Filed: May 21, 1997

Related U.S. Application Data

[60] Provisional application No. 60/018,073 May 21, 1996.
[51] Int. Cl.$^6$ .................. C07D 301/32; C07D 303/16
[52] U.S. Cl. ............................... 549/541; 547/557
[58] Field of Search ...................... 549/557, 541

[56] References Cited

U.S. PATENT DOCUMENTS

| | | | |
|---|---|---|---|
| 3,075,999 | 1/1963 | Jude et al. | 260/348.6 |
| 3,178,454 | 4/1965 | Kloos et al. | 260/348.6 |
| 4,922,002 | 5/1990 | Calbo et al. | 560/193 |
| 5,486,542 | 1/1996 | Posthuma et al. | 518/700 |

FOREIGN PATENT DOCUMENTS

SHO 46-373326  11/1971  Japan.

*Primary Examiner*—Ba K. Trinh
*Attorney, Agent, or Firm*—Blossom E. Loo

[57] ABSTRACT

A process for the distillation of the glycidyl ester reaction product of a straight or branched chain saturated monocarboxylic acid or salt thereof and an halo-substituted monoepoxide is disclosed, wherein the reaction product is subjected to conditions of temperature and vacuum in a thin film, short pass distillation apparatus such as a wiped film evaporator. The product distillate has significantly reduced color than the reaction product prior to distillation, and has improved heat and color stability.

19 Claims, No Drawings

PROCESS FOR THE PURIFICATION OF GLYCIDYL ESTERS FROM EPIHALOHYDRIN AND CARBOXYLIC ACIDS

BACKGROUND OF THE INVENTION

This application claims priority to U.S. Provisional Patent Application No. 60/018,073 filed May 21, 1996.

Field of the Invention

This invention relates to a process for the distillation of glycidyl esters to provide products having reduced color and improved color stability, and to the products so produced.

Description of Related Art

Glycidyl esters of monocarboxylic acids are well known materials which are useful as chemical intermediates in the preparation of acrylic, polyester, and alkyd resins, or as reactive diluents in the preparation of thermoset epoxy, polyester and urethane paints and coatings.

Of particular interest are glycidyl esters of aliphatic monocarboxylic acids represented by the empirical formula

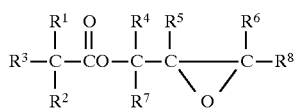

wherein $R^1$, $R^2$ and $R^3$ each represent the same or different alkyl radicals of normal or branched structure containing 1–20 carbon atoms, and $R^4$ through $R^8$ each represent hydrogen or a hydrocarbyl group containing 1–3 carbon atoms. A more preferred product is one where $R^1$ through $R^3$ are alkyl radicals containing a sum total of 3–20 carbon atoms and where $R^4$ through $R^8$ are each hydrogen, e.g., the reaction product of neodecanoic acid ($R^1+R^2+R^3=C_8$) and epichlorohydrin.

Glycidyl esters of this general type and their method of preparation are disclosed in U.S. Pat. No. 3075999, 3178454, 3275583 and 3397176, the complete disclosures of each of which are incorporated herein by reference.

Such glycidyl esters can be made by reacting an alkali salt of the carboxylic acid with a halo-substituted monoepoxide such as an epihalohydrin, e.g., epichlorohydrin (1–20 molar excess). The mixture is heated (50°–150° C.) in the presence of a catalyst forming glycidyl ester plus alkali salt and water. The water and excess epihalohydrin are removed by azeotropic distillation, and the salt by-product, e.g., NaCl, is removed by filtration and/or washing. The glycidyl esters can also be made by reacting the carboxylic acid directly with epichlorohydrin under similar process conditions. The chlorohydrin ester intermediate formed during this reaction is subsequently treated with an alkaline material, e.g., sodium or potassium hydroxide, which yields the desired glycidyl ester. By-product salt is removed by washing and/or filtration, and water is removed by drying.

Investigations of these reactions reveal that several heavier by-products are produced during the reactions to varying degrees, and species which add color to the main product are contained within the heavier by-products. The heavier by-products include the reaction products of the glycidyl ester product and/or the chlorohydrin ester intermediate with either unreacted epichlorohydrin, unreacted monocarboxylic acid or salt and/or water at various stages of the synthesis process in accordance with the following overall reaction schemes:

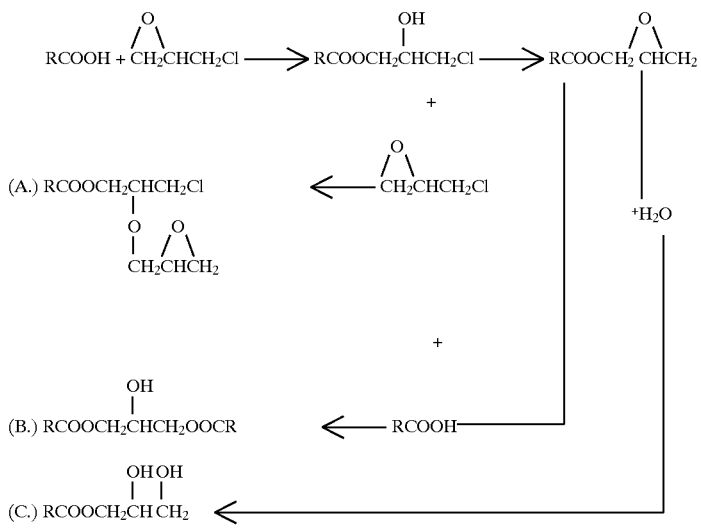

The heavier by-products may also include further reaction products of compounds A, B and/or C with the glycidyl ester product and other species present. Generally speaking, one or a combination of these or other unidentified heavies are present in the glycidyl ester reaction product at levels in excess of about 3 wt %, e.g., about 4–12 wt %.

Because glycidyl esters are thermally and chemically reactive molecules, separation of these by-products from glycidyl esters is not easily accomplished. Standard atmospheric distillation techniques have been found to increase the amount of by-products as well as the degree of color of the esters. It is believed that this increase in color is caused by the reaction at elevated temperatures, as encountered during distillation, of the glycidyl functionality present in the desired product with functionalities present in the by-products, thereby forming additional by-products. Surprisingly, standard vacuum distillation has also been found to be ineffective in reducing the initial or aged color of the glycidyl esters, and tends to worsen the color problem.

Japanese Patent 46 (1971) 37326 discloses a process for manufacturing an unsaturated organic acid glycidyl ester by reacting a salt of the unsaturated acid (acrylic or methacrylic acid) with a molar excess of epichlorohydrin. The residual unreacted epichlorohydrin is then distilled out of the reaction product using thin film distillation techniques. The resulting product is further distilled using thin film evaporation techniques to provide a purer product having improved color stability after periods of storage. The reference teaches that the process avoids the polymerization of the acrylic monomers observed during conventional distillation and thereby eliminates the need to include a polymerization inhibitor in the reaction product which inhibitor retards polymerization of the unsaturated monomers but which also reacts with the epoxy compounds to give products of less purity.

SUMMARY OF THE INVENTION

The present invention provides a process for the distillation of the glycidyl ester reaction product composition of one or more straight or branched chain saturated monocarboxylic acids or salts thereof and a halo-substituted monoepoxide comprising subjecting said reaction product composition to conditions of temperature and vacuum in a thin film, short pass distillation apparatus, and recovering a light fraction having a Pt-Co color value of less than about 100 after 20 days storage in contact with air at about 125° C., as measured by ASTM D1209.

Products produced according to the invention are of significantly reduced initial color and exhibit improved color stability after periods of storage, thereby minimizing any color contribution by these products in systems where they are used, e.g., in the preparation of alkyd, polyester or acrylic resins and especially in coating and paint formulations containing these products.

DETAILED DESCRIPTION OF THE INVENTION

Glycidyl ester products which are distilled in accordance with this invention are of the general structure set forth in formula 1 in the Background section of this disclosure, and which are the reaction product of one or a mixture of saturated monocarboxylic acids, preferably the alkali or tertiary ammonium salts thereof, and a halo-substituted monoepoxide.

Suitable saturated monocarboxylic acids which may be used to prepare the glycidyl esters are tertiary alkyl acids wherein $R^1$, $R^2$, and $R^3$ in formula 1 above each contain 1–20 carbon atoms, more preferably 1–12 carbon atoms. More preferably, the sum total of $R^1$, $R^2$ and $R^3$ is 3 to 15 carbon atoms and most preferably about 8 carbon atoms. Suitable such acids include neodecanoic, neotridecanoic, and pivalic acids. A particularly preferred acid is a neodecanoic acid prepared by the reaction of mono olefins averaging 8–10 carbon atoms in the molecule with carbon monoxide and water.

Suitable halo-substituted monoepoxides which may be used to prepare the glycidyl esters include epichlorohydrin, 1-chloro-2,3-epoxyhexane, 1-chloro-2,3-epoxy-4-butyloctane, 1-chloro-2,3-epoxy heptane, 3-chloro-4,5-epoxydodecane, 3-chloro-4,5 epoxynonane, 1-chloro-2,3-epoxy-4-cyclohexyloctane and like materials.

Glycidyl esters of this type and their method of synthesis are well known in the art and are particularly described in the aforementioned U.S. Pat. Nos. 3178454 and 3075999.

A thin film, short pass distillation evaporator is used to separate the main glycidyl ester reaction product from by-products of the A, B and/or C type as described in the Background section of this disclosure, as well as other "heavies" which may be present as impurities in the glycidyl ester reaction product. The term "heavies" as used herein means compounds or mixtures of compounds having a molecular weight higher than the target glycidyl esters. The use of such evaporators allows for rapid vacuum stripping of the glycidyl ester from the mixed reaction product without subjecting the product to excessively high temperatures or for periods of time sufficient to cause thermal degradation of the product and the further development of one or more of the heavier by-products which tend to cause coloration of the product. Typical such evaporators include shell and tube evaporators, falling or rising film evaporators and wiped film evaporators. A preferred evaporator for use in the present invention is a wiped film evaporator.

The wiped film evaporators (also referred to as agitated thin-film evaporators) preferred for use in the distillation process of the present invention are known in the art and are available commercially. A general discussion of the principle of operation of these evaporators may be found in the publication: "Agitated Thin-Film Evaporators: A Three Part Report", Parts 1 to 3; A. B. Mutzenburg, N. Parker and R. Fischer; Chemical Engineering, Sep. 13, 1965.

Typically, wiped film evaporators comprise a cylindrical evaporating vessel. The vessel may be either vertical or horizontal, with vertically arranged vessels being preferred. The evaporator further comprises a rotor mounted within the cylindrical evaporating vessel and provided with a number of wiper blades, and a motor is provided to drive the rotor. The rotor is arranged within the cylindrical evaporating vessel so that, upon rotation by the motor, the wiper blades are caused to move over the inner surface of the cylindrical vessel. The wiper blades may contact the inner surface of the cylindrical vessel or, alternatively, a small gap or clearance may be left between the tips of the wiper blades and the inner surface of the cylindrical vessel.

In operation, the mixture to be separated is fed, supplied or subjected to the evaporator and forms a thin film over the inner surface of the cylindrical vessel. The film is heated, typically by means of indirect heat exchange with a heating medium through the wall of the cylindrical vessel, such as steam. The action of the wiper blades in passing over the surface is to agitate the film of the glycidyl ester composition which forms on the inner cylinder surface, resulting in turbulence in the film, which in turn improves heat and mass transfer. In addition, the wiper blades insure an even distribution of the composition over the inner surface of the vessel and prevent channeling of the liquid as it passes across the surface. Under the action of the wiper blades and the heating, the lighter components of the mixture are caused to evaporate.

The light product is removed from the evaporator as a vapor and is subsequently condensed. Condensing is conveniently effected by indirect heat exchange with a cooling medium such as water. The condenser may be separate from the evaporator vessel or may be located within the vessel. In the latter case, the vessel will comprise a first evaporating section in which the rotor and wiper blades are arranged and a second condensing section in which the condenser is housed. If desired, a separating section may be disposed between the evaporating section and the condensing section to allow removal of any liquid droplets entrained in the vapor prior to condensing.

The heavy product is removed from the evaporator as a liquid flowing from the inner surface of the cylindrical vessel. The wiped film evaporator is operated under a vacuum. Suitable pumps for the generation and maintenance of the vacuum are well known in the art. Typical examples of suitable pumps include steam ejector pumps and diffusion vacuum pumps.

According to the process of the present invention, the mixture to be separated is first heated to a temperature sufficient to reduce the viscosity of the mixture, thereby allowing it to more readily flow. The mixture is then introduced into the evaporator to form a thin film on the inner surface of the heat exchanger surface of the evaporator vessel, e.g., a cylindrical drum or a series of tubes. The operating pressures for the thin film evaporator will vary according to the precise nature of the ester feedstock. Typical operating pressures are in the range of about 0.05 to about 50 mm Hg, more preferably from about 0.5 to about 5 mm Hg. Typical operating temperatures in the evaporator will be in the range of from about 100° C. to about 200° C., more preferably from about 115° C. to 175° C. The average residence time of the glycidyl ester reaction product composition in the evaporator is relatively low as compared with that of a conventional batch distillation apparatus, and this is believed to be a key factor in the avoidance of discoloration of the distillate. Typical average residence time is in the range of from about 0.2 to about 10 minutes, more preferably less than about 2 minutes, depending upon the nature of the feedstock and the design of evaporator being employed. It is important, however, that the operating temperature is not so high as to lead to a substantial degree of thermal degradation of the mixture being processed at the particular residence time and that the operating conditions of temperature and pressure are selected to ensure that such high temperatures are not required.

Suitable wiped film evaporators which may be used in accordance with this invention include apparati of the type disclosed in U.S. Pat. Nos. 3878029, 4160692 or 4173246.

Preferred glycidyl esters purified in accordance with this invention will generally exhibit boiling points in the range of from about 110°–125° C. at 8 mm Hg and a content of by-products such as A, B and/or C described in the Background section of this disclosure of less than 4 wt %, more preferably less than 2 wt % and most preferably less than 0.5 wt %. Coloration of the distilled product is in many cases reduced at least 50%, more preferably at least 60%, compared with the product coloration prior to distillation, as measured using the Pt-Co scale in accordance with ASTM test method D 1209. Glycidyl esters purified in accordance with this invention generally exhibit initial Pt-Co color values of less than 40 units prior to heat storage, more preferably in the range of 5–30 Pt-Co units, and values of less than about 100 Pt-Co units after 20 days storage in air at about 125° C., or values of less than about 50 Pt-Co units after 20 days storage under an inert gas such as nitrogen at about 125° C. These products also exhibit an at least about 3% reduction in epoxy equivalent weight (EEW) as compared with the non-purified starting material, more preferably a 4 to 8% reduction in EEW.

The following examples are illustrative of the invention.

EXAMPLE 1

A commercially available glycidyl ester of neodecanoic acid and epichlorohydrin marketed by Exxon Chemical Corporation under the tradename GLYDEXX® ND-101 was provided. This material has an atmospheric boiling point in the range of about 250° C. to 280° C. and a content of by-products "heavies" of about 10 wt %. Five hundred grams of the starting glycidyl ester was fed through a Pope Scientific Model 40450 two inch molecular still (cylinder) equipped with carbon wiper blades. The still temperature was maintained at 115° C. and the pressure was 3 mm Hg. Flow rate of the ester was maintained at 80–100 g/hr. The overhead distillate was condensed and collected, yielding a total of 466.1 grams of overhead and 30.7 grams of non-distilled bottoms. The distillate and starting material were analyzed by gas chromatography using a Hewlett Packard 5890 instrument equipped with a 1 micrometer DB-1 column. Analysis of the distillate showed about a 50% reduction of the heavier ends (heavies) as compared with the glycidyl ester prior to distillation as shown in Table 1 and a reduction of the epoxy equivalent weight (EEW) from 254 to 241. The latter was measured in accordance with a modification of ASTM method D1652B.

TABLE 1

Gas Chromatography Analytical Results

| Peak Assignment | Retention Times minutes | Starting Material (area %) | Distillate (area %) |
|---|---|---|---|
| Lights | 5.4–34.7 | 2.04 | 2.01 |
| Glycidyl Ester Product(1) | 34.7–44.0 | 88.29 | 93.34 |
| Heavies(2) | 44.0–56.3 | 9.67 | 4.65 |

(1)Includes glycidyl neononanoate, glycidyl neodecanoate, glycidyl undecanoate, Compound C and chlorohydrin ester intermediates peaks
(2)Includes Compounds A and B peaks.

One of the particular advantages afforded by the purification process of this invention is a reduction in the EEW of the purified glycidyl ester product as compared with the starting product. For example, the product of Example 1 shows about a 5% EEW reduction (from 254 to 241) which is indicative of a more highly purified product. The theoretically pure product would have an EEW of about 228. A lower EEW means a higher epoxy concentration in the product which leads to greater efficiency when these glycidyl esters are used as resin modifiers or reactive diluents in other polymer systems.

EXAMPLE 2

Color comparisons of the pre-distilled and post distilled glycidyl ester composition were performed in accordance with ASTM-D1209. Also, the resistance to further discoloration of the glycidyl esters was evaluated in a heat stability test. For this test, approximately 125 ml samples of glycidyl esters were placed in 8 ounce jars. The jars were covered with foil-lined phenolic caps which were further secured with electrical tape. The sealed jars were about one-half full of glycidyl ester and one-half full of air. They were placed into a 125° C. oven which was continuously purged with nitrogen. After a few days, the jars were removed from the oven and allowed to cool about 1 to 2 hours. Colors of the samples were then measured via procedures described in ASTM D1209. This procedure was repeated with the heat aged samples up to a total heating period of 20 days. Results of color comparisons between the non-distilled product and the product distilled in accordance with Example 1 are shown in Table 2.

TABLE 2

| DAYS HEATED | NON-DISTILLED | EXAMPLE 1 |
|---|---|---|
| | color (Pt—Co Scale) | |
| Initial Samples | 50 | 10–15 |
| 2 | 50–60 | 15 |
| 4 | 50 | 15–20 |
| 6 | 50–60 | 15–20 |
| 8 | 45–50 | 20 |
| 10 | 45–50 | 20 |
| 20 | >250 | 80–90 |

The results in Table 2 show that the initial color of the GLYDEXX® product (50 Pt-Co units) was reduced to 10–15 Pt-Co units after the product was distilled in accordance with Example 1. The distilled product also demonstrated remarkable color stability after aging in air up to 20 days as compared with the starting product.

We claim:

1. A process for the distillation of the glycidyl ester reaction product composition of one or a mixture of saturated monocarboxylic acids or salts thereof and a halo-substituted monoepoxide, comprising subjecting said reaction product composition to conditions of temperature and vacuum in a thin film, short pass distillation evaporator and recovering a purified glycidyl ester light fraction having A Pt-Co color value of less than about 100 after 20 days storage in contact with air at about 125° C., as measured in Pt-Co units in accordance with ASTM D1209 and containing less than about 4 wt % of molecular species heavier than said purified glycidyl ester.

2. The process of claim 1 wherein said light fraction has the formula:

$$R^3-\underset{\underset{R^2}{|}}{\overset{\overset{R^1}{|}}{C}}-\overset{\overset{O}{\|}}{C}O-\underset{\underset{R^7}{|}}{\overset{\overset{R^4}{|}}{C}}-\overset{\overset{R^5}{|}}{C}\underset{O}{\overset{R^6}{\diagdown\diagup}}C-R^8$$

wherein $R^1$, $R^2$ and $R^3$ each represent the same or different alkyl radicals of normal or branched structure containing 1–20 carbon atoms and $R^4$ through $R^8$ each represent hydrogen or a hydrocarbyl group containing 1–3 carbon atoms.

3. The process of claim 2 wherein $R^1$, $R^2$ and $R^3$ are alkyl radicals containing a total of 3–20 carbon atoms and $R^4$ through $R^8$ are each hydrogen.

4. The process of claim 2 wherein $R^1$, $R^2$ and $R^3$ contain a total of about 8 carbon atoms.

5. The process of claim 1 wherein said evaporator is a wiped film evaporator.

6. The process of claim 1 wherein said film evaporator is operated at a temperature in the range of from about 100° C. to about 200° C.

7. The process of claim 1 wherein said film evaporator is operated at a pressure in the range of from about 0.05 to about 50 mm Hg.

8. The process of claim 1 wherein the average residence time of said reaction product in said evaporator is in the range of about 0.2 to about 10 minutes.

9. The process of claim 5 wherein said wiped film evaporator is operated at temperatures in the range of about 115° to 175° C., a pressure in the range of about 0.5 to 5 mm Hg and wherein the average residence time of said reaction product in said evaporator is less than 2 minutes.

10. A purified glycidyl ester product having the formula:

$$R^3-\underset{\underset{R^2}{|}}{\overset{\overset{R^1}{|}}{C}}-\overset{\overset{O}{\|}}{C}O-\underset{\underset{R^7}{|}}{\overset{\overset{R^4}{|}}{C}}-\overset{\overset{R^5}{|}}{C}\underset{O}{\overset{R^6}{\diagdown\diagup}}C-R^8$$

wherein $R^1$, $R^2$ and $R^3$ each represent the same or different alkyl radicals of normal or branched structure containing 1–20 carbon atoms and $R^4$ through $R^8$ each represent hydrogen or a hydrocarbyl group containing 1–3 carbon atoms, said product having a Pt-Co color value of less than about 100 after 20 days storage in contact with air at about 125° C., as measured in Pt-Co units in accordance with ASTM D1209 and containing less than about 4 wt % of molecular species heavier than said purified glycidyl ester product.

11. The product of claim 10 which is a purified glycidyl ester product having at least about 50% reduced coloration compared with said glycidyl ester product prior to purification.

12. The purified product of claim 11 which has an initial Pt-Co color value of less than 40 prior to said storage.

13. The purified product of claim 12 which has an initial Pt-Co color value in the range of about 5 to 30 prior to said storage.

14. The purified product of claim 10 which has a Pt-Co color value of less than about 50 after 20 days storage in contact with nitrogen at about 125° C.

15. The purified product of claim 11 which has an at least about 3% reduction in epoxy equivalent weight as compared with said product prior to purification.

16. The purified product of claim 15 which has about a 4 to 8% reduction in epoxy equivalent weight as compared with said product prior to purification.

17. The purified product of claim 11 which contains less than 2 wt % of molecular species heavier than said purified glycidyl ester product.

18. The purified product of claim 17 which contains less than 0.5 wt % of molecular species heavier than said purified glycidyl ester product.

19. The product of claim 10 wherein $R^1$, $R^2$ and $R^3$ contain a total of about 8 to 10 atoms and $R^4$ through $R^8$ are each hydrogen.

* * * * *